US007257832B2

(12) United States Patent
Beane et al.

(10) Patent No.: US 7,257,832 B2
(45) Date of Patent: Aug. 14, 2007

(54) MEDICAL IMAGE CAPTURE SYSTEM AND METHOD

(75) Inventors: John A. Beane, Carlsbad, CA (US); Larry J. Heminger, Oceanside, CA (US); Robert M. Stone, Santa Monica, CA (US)

(73) Assignee: Heartlab, Inc., Westerly, RI (US)

( * ) Notice: Subject to any disclaimer, the term of this patent is extended or adjusted under 35 U.S.C. 154(b) by 662 days.

(21) Appl. No.: 09/974,406

(22) Filed: Oct. 9, 2001

(65) Prior Publication Data
US 2002/0073429 A1 Jun. 13, 2002

Related U.S. Application Data

(60) Provisional application No. 60/240,681, filed on Oct. 16, 2000.

(51) Int. Cl.
H04N 7/173 (2006.01)
(52) U.S. Cl. .................. 725/105; 348/61; 348/143
(58) Field of Classification Search ............ 725/105; 348/61, 143, 159, 161; 358/1.14; 715/719; 705/3
See application file for complete search history.

(56) References Cited
U.S. PATENT DOCUMENTS
5,619,995 A  4/1997 Lobodzinski ............ 128/653.1

6,272,470 B1 * 8/2001 Teshima ..................... 705/3
6,381,029 B1 * 4/2002 Tipirneni .................. 358/1.14
6,573,907 B1 * 6/2003 Madrane .................... 715/719

FOREIGN PATENT DOCUMENTS
WO    WO 00/33231    6/2000
WO    WO 00/57339    9/2000
WO    WO 00/60522    10/2000

* cited by examiner

Primary Examiner—Allen Wong
(74) Attorney, Agent, or Firm—Houston Eliseeva LLP

(57) ABSTRACT

As patient video images are captured in a lab, they are converted into an uncompressed data set and stored locally on a hospital site server, where they are immediately viewable by diagnosticians in the hospital. The hospital site server generates a plurality of compressed data sets for use by the Internet Data Center. Additionally, the uncompressed data set and a plurality of compressed data sets are stored permanently on a centralized Internet Data Center, from which they can be searched out and displayed by any client device running web-browser software. A client is provided with immediate access to the uncompressed images when pausing and requesting the images of interest from the server. The patient video images are automatically delivered to any authorized Clinical Research Organizations, they are delivered back to the treating hospital when the patient returns for subsequent visits, and are viewable through in-hospital viewing stations over a private high-speed network.

14 Claims, 5 Drawing Sheets

Hospital Site Server

Hospital Review Station

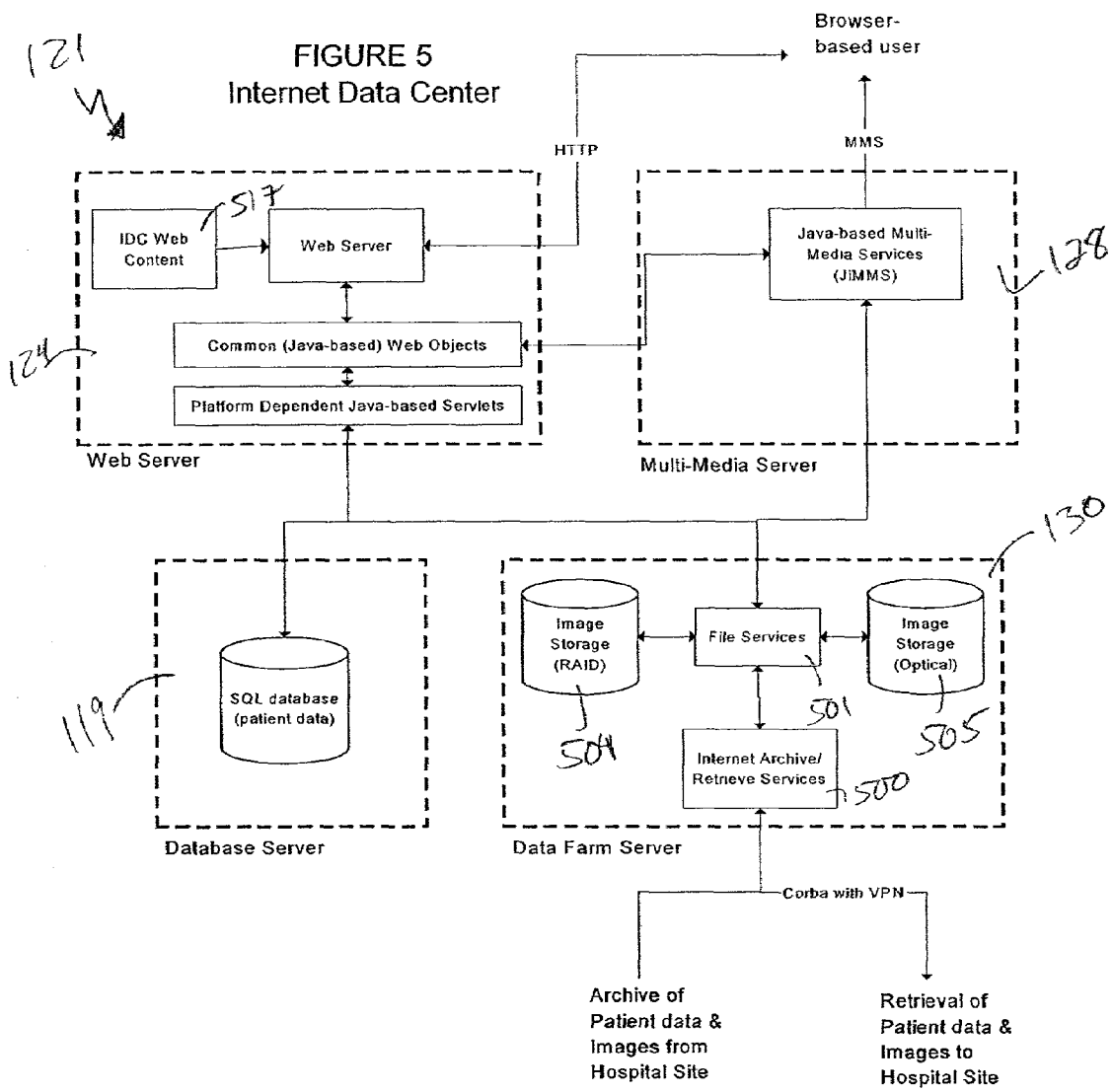

MEDICAL IMAGE CAPTURE SYSTEM AND METHOD

RELATED APPLICATIONS

This application claims priority to U.S. Provisional Application No. 60/240,681 filed on Oct. 16, 2000.

BACKGROUND OF THE INVENTION

1. Field of the Invention

The invention relates to systems and methods for collecting medical video images of a patient and delivering the video images to a remote station. More specifically, the invention is directed to a system and method for transferring cardiac video images with negligible image degradation, archiving the images in long-term storage media, and providing a streaming multi-media video file that allows medical diagnosis and collaboration by doctors located outside the immediate treating hospital.

2. Description of the Related Art

Current advances in technologies related to compression, storage, and retrieval of digital video data are making their way into the medical field. These advances are making digital storage and display an economical means for hospitals and doctors to archive and review patient records. The scope of economic feasibility extends to cost, time, and image quality.

Traditional methods of archiving patient records involve substantial costs incurred from the physical media and allocating shelf space to store the same. Traditional paper and film storage methods require a significant amount of space, oftentimes requiring an entire filing room to store the accumulation of data. Newer digital methods of storing patient information require a system of removable high-capacity storage devices, such as tape drives, magneto-optical disk drives and recordable compact disks, which require a significant amount of cost and time to file and retrieve.

The time required to file and retrieve physical media in a storage facility is cumbersome, as a filing clerk is required to understand the filing structure, find the correct digitally recorded media, and then deliver the media to the diagnostician requesting the record.

Currently, archiving of patient video images is often performed with analog means, such as 35 mm black and white cine' film. Archiving and retrieving of such films are expensive and cumbersome. First of all, there is a significant cost associated with the chemicals required to develop the film. These chemicals must be kept at a specific temperature, and they break down over a short period of time. The chemicals must be replaced frequently, or there is a risk of compromising the quality of the medical image. This results in a higher cost for facilities with low volume. Secondly, this requires the creation and maintenance of a storage facility at optimum atmospheric conditions to preserve the film. Thirdly, the space required to store large numbers of film canisters takes up a significant amount of space. Hospitals would prefer to use this space for revenue generating purposes, such as patient rooms or labs. Finally, the process of reviewing a linear film to find a particular physiological event is time consuming.

In addition to cine' film, another method of recording analog video data is to incorporate a professional grade videotape recorder into the image acquisition system. A serious disadvantage of this method, like the cine' film, is the tedious searching along the linear videotape to find a specific physiological event a diagnostician wishes to view. Playback requires special commercial grade videotape players. These are expensive and are not typically available in each of the many locations in a building where a physician may wish to review the image data. This forces the physician to seek out the player. In a situation where the physician needs to consult the images before treating the patient, it is always possible he or she will be interrupted on the way back to the patient, thus affecting his or her retention of the image. Another inherent disadvantage is the physical size of the videotape and the storage area necessary to harbor large quantities of patient information. Still another disadvantage is the fact that any relevant patient demographic information is only available visually and does not allow electronic databasing for quick retrieval. Thus, videotape is not an ideal solution to storage and retrieval of medical video images.

Many medical personnel have desired a digital means of archiving, searching, retrieving and viewing patient video data. There are current digital systems that allow digital video data to be recorded on transportable media such as magneto-optical or recordable optical compact discs. These systems provide transportable media with the ability to efficiently store large amounts of video data and methods for viewing the video images through a display device, such as a video monitor. However, there are still considerable drawbacks in current digital archiving systems.

An inherent problem associated with digital storage of medical video data is the file size that can be many megabytes per procedure. Files of these sizes can require a large amount of bandwidth, storage space, and memory. Thus, compression techniques become imperative when dealing with digitized video data. Image compression is usually accomplished in one of two ways. First is the intra-frame technique, wherein the compression takes place within each individual frame. Color depth may be reduced, image size altered, or resolution decreased to achieve an acceptable file size. An alternative method is the inter-frame compression technique, wherein compression is accomplished between frames. Multiple frames that do not significantly change from one to the next may be collapsed into a single frame that is then displayed during the time normally reserved for previous collection of frames.

In dealing with medical images, image quality is normally more important than file size. Unlike other types of multi-media applications, medical applications require detailed images since those images are often the basis for medical diagnoses. The original image quality is often termed lossless, denoting that there is no loss between the original image and the digitized version. Images that have undergone compression are labeled lossy images, denoting that some image quality has been lost due to compression. Many current compression techniques can slightly compress images with negligible image degradation. Unfortunately, the inherent sacrifice with compression is that as compression ratios are increased, image quality is decreased. Therefore, it is imperative that any compression results in negligible image degradation, and that the lossless images are immediately available for viewing.

Several systems have been implemented for compressing medical video images and then archiving them to digital media. One such system is disclosed in Lobodzinski, U.S. Pat. No. 5,619,995, which discloses a system for combining diagnostic digital motion video acquisition, display, and processing with physiological data indexing through utilization of techniques of digital motion video compression through domain transformation.

While some of the prior art systems allow for video storage, many of these systems require the doctor to have access to, or a copy of, the removable storage media. This is inefficient because without additional copies, only one physician can view the video data at a time, and viewing the data from a remote location requires video data media to be mailed or transmitted electronically such as through e-mail. This is a time consuming process that requires a large amount of storage space due to the large image file sizes. Moreover, either method of delivering video data to a remote location is critically deficient when a doctor must immediately diagnose a patient condition and does not possess the storage media or have the data saved locally on a computer.

Additionally, it may be desirous that organizations other than the hospital have access to patient video data. One such organization is a clinical research organization. Unfortunately, it is tedious and costly to make copies of digital video media and mail them to the various organizations requiring the patient video data.

What is needed is a system that provides physicians with a convenient way to view patient video data from remote locations. Additionally, it is desirous for a system to allow sharing of a single video data file from multiple locations simultaneously. Furthermore, a storage media that does not require a substantial amount of space or retrieval time would greatly enhance the benefits of digital archiving.

SUMMARY OF THE INVENTION

Embodiments of the invention relate to a system that captures, stores and transmits video images such as those taken during a cardiac catheterization procedure. As video data are captured through a video input device, such as an X-Ray Angioplasty Machine, it is combined with patient demographic information, such as patient name and ID, in an acquisition station. The acquisition station captures and stores the video data in a format such as a Digital Imaging and Communications in Medicine (DICOM) data set. Each data set typically corresponds to several runs of a particular catheterization procedure. Thus, one "set" provides several related video images.

The acquisition station converts any analog images from the video camera into digital data. The acquisition station then sends the resulting DICOM data set through a high speed data network to a site server computer that may be located at or near the acquisition station, such as within the same hospital. This process is performed automatically and almost instantaneously following input of the patient demographic information and capturing of the patient video data from a procedure such as cardiac angioplasty. Thus, patient video data becomes immediately accessible by other practitioners having data links to the site server.

The site server temporarily stores the "lossless" DICOM data set locally and allows practitioner's in the hospital to view the DICOM data sets through in-hospital review stations that are connected to the private high speed network. The DICOM images are termed "lossless" because no compression is used to store these files.

Once the site server receives the DICOM data sets from a series of patient procedures, a "thumbnail" image representing each patient procedure is generated and stored along with the DICOM data set. Advantageously, the thumbnail image is preferably taken from a center frame of a video procedure. Because the die or contrast media used during, for example, a cardiac catheterization procedure is not as apparent in either the beginning or ending frames, taking a thumbnail image from the center frame is more likely to be an accurate representative image of the procedure.

After a thumbnail image has been created, instructions within the site server generate different compressed video files from the DICOM file. Each procedure video is preferably used to generate three separate video files that are compatible with a computer video display program, such as the QUICKTIME player from Apple Computer, Inc. The three video files are preferably generated with differing amounts of compression so that they can be played to end users across various bandwidth links. For example, an end user with a low bandwidth connection to the site server would want to view a highly compressed file, even through some loss of video quality will result from the high compression. However, an end user with a high bandwidth connection would want to view a procedure video that is only slightly compressed so that they can receive the highest video quality.

Once the compressed video files have been generated they are automatically sent using a secured encrypted virtual private network (VPN) connection to a server within a central Internet data center (IDC). In addition, the DICOM data sets are also sent at the same time, or a later time, to the IDC. Advantageously, the DICOM data sets are sent when bandwidth requirements on the IDC are detected to be low, such as late at night or on weekends. Since most users will request the compressed files, and not review the DICOM data sets, it is not necessary to send them immediately to the IDC.

Furthermore, the Internet data center includes, or is in communication with, a database server that is configured to index and search the archive of DICOM data sets, which makes any compressed video file or DICOM data set available to a web-based client running web-browser software. When a web-based client requests a video file from a particular procedure, the IDC preferably detects the web-based client's bandwidth. A multi-media server is then able to deliver the appropriately compressed image file as a streaming multi-media file to the end user.

As the end user views the procedure video, the player preferably provides an option for stopping the image at a selected video frame. Once the viewer has been stopped, the reviewer can then select a particular frame of interest using a keystroke or the mouse. Once this happens, the player sends a message to a computer within the IDC with the identification of the video being played and the frame of interest. The computer within the IDC then determines the lossless DICOM file that corresponds to the video being reviewed and determines the frame of interest within the lossless DICOM file. Once the frame of interest within the DICOM file has been identified, approximately 5-10 frames before and after the frame of interest are stored to a new lossless video file. These lossless video frames are then sent to the reviewer so that approximately 10-20 frames of very clear, lossless images from video procedure can be reviewed.

One efficient method for streaming media provides for an IDC server to calculate the client's bandwidth and thereafter determine the number of video frames to skip in order to show the full video procedure loop without having to wait for each successive frame to load. Conventional video download systems will skip a fixed number of frames as the video is streamed to a player at the end user's computer. This allows the video image to begin playing, albeit roughly, almost immediately upon a user requesting to view the video. These systems, for example, will send video frames 1, 10, 20, 30 . . . etc. until the end of the video is reached.

These frames are stored on the end user's system and played as a jerky video. Conventional systems then send frames 2, 11, 21, 31 . . . etc to the end user. This video will be less jerky than the previous version. This process continues until all of the frames have been downloaded.

In one embodiment of the invention, video streams are ordered so that the frames are sent in sequential order. However, the frames are ordered such that the video loop contains frames that are out of sequence in comparison to the originally captured video. For example, a video with 10 frames can be ordered 1, 5, 10, 2, 6, 3, 7, 4, 8, 9. This would show the video as jerky while only frames 1, 5 and 10 have been loaded, but would become more smooth as the additional frames in the file "fill in" the frame gaps. This is more efficient than prior systems because no frames are actually skipped as the frames are downloaded. Accordingly, the entire order of the frames within the video is reordered such that the server may deliver the frames sequentially from the stored file without having to skip a certain number of frames between each frame download.

In another embodiment of the invention, a hospital site server automatically sends each created DICOM video file, and the compressed versions of the video file to a computer at a Clinical Research Organization that has permission to receive such file. This facilitates the sharing of lossless DICOM data without manual intervention required to download and save the data. Of course, the DICOM file could alternatively be first transferred to the IDC, which then forwards the file to the Clinical Research Organization. Using this embodiment a Clinical Research Organization will have the requested files available when they are ready to view them, without having to wait for a lossy DICOMDIR file to download. Additionally, a patient that is entered into several clinical trials might have his cardiac data sent to multiple clinical research organizations.

In order to overcome the noted deficiencies in the prior art, aspects of the system described herein capture patient video data and combine it with patient demographic information into a single patient data file that is archived within a searchable database.

One aspect of the invention allows the patient data file to be immediately accessed by other diagnosticians outside the immediate laboratory.

Yet another aspect of the invention relates to automatically archiving and storing each patient data file for long-term storage and retrieval from a central database server.

Still another aspect of the invention allows remote access to any patient data file from any device running web-browser software.

In another embodiment, a compressed patient video data file is stored with varying compression ratios, or no compression at all, to archive a plurality of patient data files for later retrieval by devices with varying bandwidths.

One other aspect of the invention provides multi-media streaming of the patient data file over the Internet, wherein the compression ratio of the multi-media stream is dependent upon the user's calculated bandwidth. In the future, as bandwidth speeds increase and costs come down, no compression of the original image may be required.

Still another aspect of the invention is automatically delivery of the patient video data file to a Clinical Research Organization, without that organization being required to download the file from the Internet.

Yet another aspect of the invention is a video player that provides palindrome viewing capabilities. That is, the ability to play the video images in forward or reverse. Additional functionality of the player allows the video to be paused, to loop certain frames, and to capture compressed or lossless still images from the video images. Moreover, the system is provided with image enhancing features specifically designed for medical images. For example, the video player includes tools for: zooming, edge enhancement, smoothing, sharpening, altering brightness, altering contrast, gamma correction, and other filters or enhancements that provide a better image to the reviewing physician.

A further aspect of the invention is a video player that allows the compressed video images to be paused and then to retrieve the corresponding lossless images for better diagnostic purposes. Furthermore, when a diagnostician clicks on an image frame of interest, the player grants immediate access to the lossless frame data, plus several lossless frames on either side of the frame of interest, for viewing lossless video data.

Additionally, a diagnostician can request a loop of lossless video images corresponding to a lossy video loop currently being viewed.

Yet another aspect of the invention is a server that is configured to automatically retrieve the archived lossless video data from a central IDC storage when a patient returns to the hospital so a doctor can have immediate access to the lossless data for reviewing.

Further objects of the invention will become apparent from the following drawings and description.

BRIEF DESCRIPTION OF THE DRAWINGS

FIG. 5 is a block diagram illustrating one embodiment of an Internet Data Center.

DETAILED DESCRIPTION OF THE INVENTION

Figure 1:
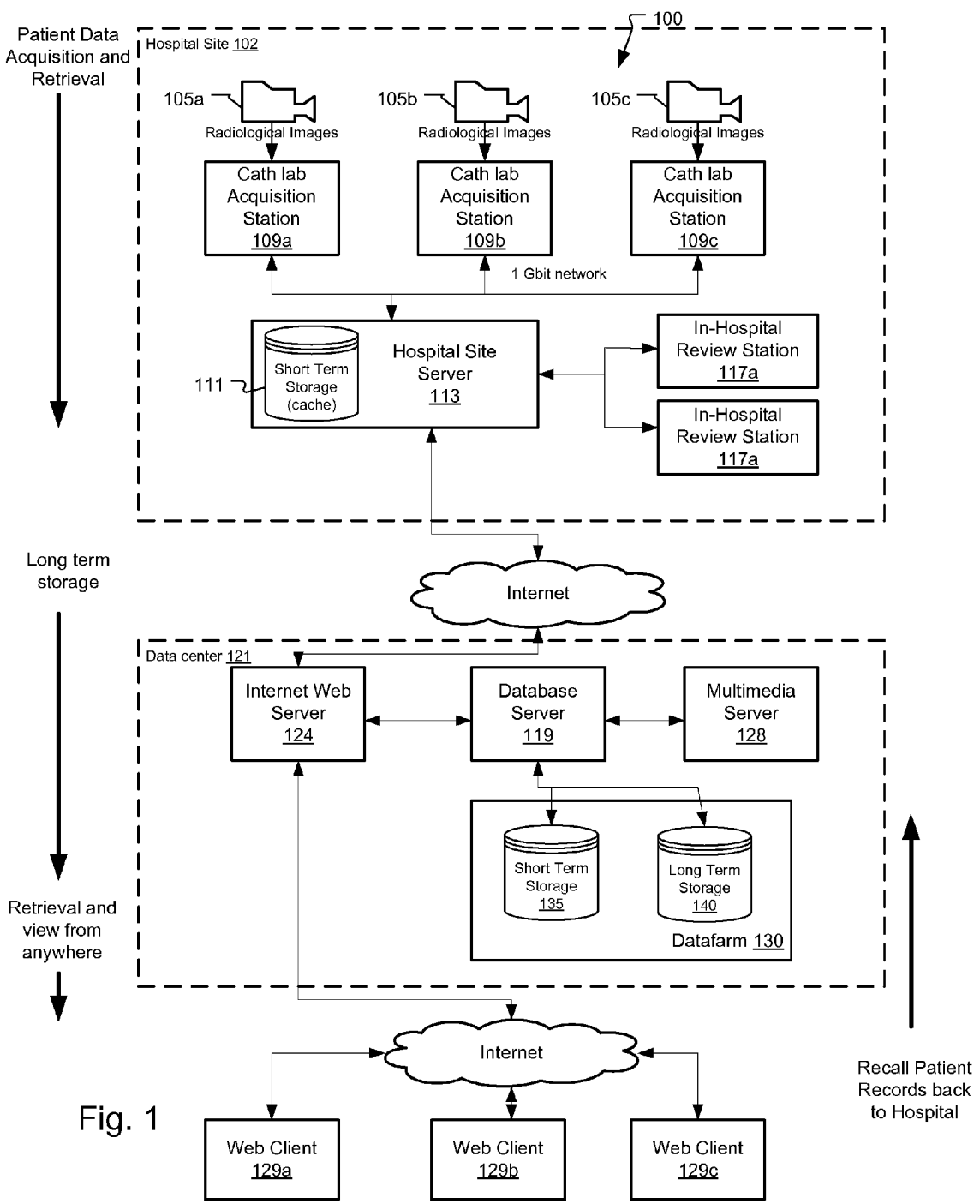
FIG. 1 is a block diagram showing the components of one embodiment of a video capture system.

The following detailed description discusses the invention utilized in conjunction with captured medical images.

A. Overview

In one embodiment inside a hospital, a medical image system makes use of three differing technologies: (1) The DICOM video standard, (2) Analog image capture, and (3) High speed (Gigabit), local area networking. DICOM, an acronym for Digital Information and Communications in Medicine, is commonly used by a majority of medical imaging applications. DICOM defines both an image file format as well as a network protocol, enabling imaging and acquisition products from a variety of vendors to interoperate. For a more complete discussion of the DICOM standard itself, please refer to the following resources:

Radiological Society of North America (RSNA)—A Non-Technical Introduction to DICOM: http://www.rsna.org/REG/practiceres/dicom/nontechintro.html National Electrical Manufacturers Association (NEMA)—The DICOM Standard: http://medical.nema.org/dicom.html In embodiments of the system, cardiology images conforming to the DICOM standard are taken directly from digital catheterization lab equipment and stored on a Site Server within the hospital. The Site Server acts as a cache for local DICOM images captured over the most recent few weeks or months, and may be integrated with any vendor's catheterization camera equipment so long as the camera equipment conforms to the DICOM networking standard. Of course, it should be understood that DICOM is only one standard for capturing and transmitting lossless image data. Embodiments of the invention are not limited to this one standard, and are anticipated to function similarly using differing video standards.

Images conforming to the DICOM standard are also preferably used by an In-Hospital Review Computer Station to import and/or upload a DICOM compliant CD (compact disc) to the Site Server, and to export selected video studies from the system to a DICOM CD. Using video images in this manner, the system can import, export and display cardiology images to/from any other vendor's equipment.

In order to acquire images from legacy film-based systems (without digital DICOM capabilities), the system includes an Analog Image Acquisition Station. Using real-time image capture technology, the Image Acquisition Station converts the output of a catheterization camera directly to digital format, compresses the image using a JPEG lossless algorithm, and finally converts the output to DICOM format. Starting and stopping of analog image acquisition is preferably controlled from a foot pedal attached to the catheterization lab system. The resulting DICOM images are sent to the Site Server in the same manner as a digital DICOM acquisition. Using this technique, the system supports hospital sites using a combination of digital and analog image capture without difficulty. Frame rates up to 60 images per second are supported.

Finally, the Site Server, Review Station(s) and Image Acquisition Station(s) are preferably connected together using a high-speed gigabit local area network (LAN). This gigabit LAN is 10 to 100 times faster than a normal Ethernet LAN, and provides near instantaneous access to any selected study and/or image from any Review Station. The gigabit LAN is preferably a private segment, and thus it will not impact or impede data traffic across the existing in-hospital network.

1. Secure Archival Services

From the Site Server within the hospital, patient records and image files are archived to an Internet Data Center (IDC) over the public Internet. This Internet link is preferably configured at T1 data rates (1.54 Mbps) or faster with an automatic archival process. Accordingly, no user intervention is required to "push" data from the hospital to the IDC.

Using Virtual Private Network (VPN) technology, the connection between each hospital site and a central IDC is secure, safe and reliable. Commercially available VPN hardware and/or software is installed at each hospital site, between the Site Server and the Internet interface, allowing only authorized communication to take place. The VPN is preferably configured to require user-level authentication as well as a high level of data encryption, such as triple-DES (3DES). A high performance VPN concentrator can be located at the IDC and configured to communicate only with authorized hospital sites.

The VPN concentrator will not allow access to the IDC from any other location, or from any other user. Data transmitted between the hospital sites and the IDC is encrypted using the highest level available (128-bit), such that it is unlikely to be intercepted, deciphered, or otherwise compromised. Encryption and decryption keys are preferably rotated periodically and automatically.

2. Secure Web Access

Once archived at the IDC, patient data and cardiology images are available almost instantaneously from a web-browser based application. An authorized and authenticated user may login to a web server within the IDC and quickly browse studies of interest. In addition, compressed streaming versions of cardiology image(s) are available using an Apple QuickTime® player. Of course, embodiments of the invention are not limited to the Quicktime viewer. For example, other commercial or custom viewers that support advanced image processing features are also within the scope of the invention. If the user has a broadband Internet connection (DSL or greater speeds), the quality of the streaming images is remarkably similar to fill DICOM resolution.

Using various compression techniques, the lossless DICOM images originally captured from the catheter camera (either analog or digital) are converted to a compressed streaming file format automatically and transparently to the user. There is minimal latency between the time a user clicks a desired image, and the streaming image begins to appear on the screen.

Integration between the web-browser and the IDC is accomplished in the background using, for example, JAVA based programming technology in combination with Oracle Corporation's 8i enterprise level relational database product It should be realized that other database products, such as the Microsoft SQL server could also be used without departing from the scope of the invention.

Secure web access is provided using a combination of digital certificates and Secure Sockets Layer (SSL) technology. First, a digital certificate is acquired from a leading industry source specializing in Internet Trust Services (e.g. Verisign, RSA, etc.) and is installed on each authorized server computer. When accessing this server, the user's web browser will verify the digital certificate with the Trust Service in order to make sure the user is communicating with the proper server. Once the server is authenticated, the user is asked to login to the system using a combination of account name, password and Site Id. Thus, both server and user authentication must take place prior to accessing any of the IDC data.

Finally, once both server and user are authenticated, all data transmitted between the client (web browser) and the server is encrypted using, as one example, 128-bit Secure Sockets Layer (SSL) technology. SSL is built into most modem web browsers, and provides transparent encryption and decryption of the data. This is the same level of data encryption provided by the VPN (discussed above), but SSL is integrated into the web browser providing ease of use.

3. Internet Data Center

The Internet Data Center (IDC) is the long-term repository for patient records, cardiology images, and compressed steaming images. Technology deployed at the DC has been selected for its ability to afford high availability, reliability and its ability to scale to handle the amount of storage required. This technology includes such equipment as RAID (high speed and high capacity disk storage), Storage Area Network (SAN), robotic optical storage jukeboxes, and robotic tape back-up for disaster recovery.

The IDC is designed with reliability and redundancy in mind and thus employs multiple, redundant internal networks and servers such that there is no single point of failure. The IDC server computers are protected by high performance network routers, firewalls and VPN concentrators. This network equipment protects the IDC and its data from unauthorized access and use, as well as from malicious intrusions. The database in the IDC is preferably powered by an Oracle database, providing a highly scalable enterprise relational database solution.

B. System

As discussed above, embodiments of the system relate to an image capture system for obtaining, storing and playing medical images. The medical images are preferably medical video images, but could also be static digital images in well-known formats such as GIF, JPG and TIFF. The medical images are preferably captured as part of a cardiac catheterization procedure, but can also include images captured from other diagnostic imaging devices, such as CT, MRI, IVUS, ultrasonography, x-ray systems, and the like.

In reference to FIG. 1, a medical imaging system 100 and its sub-components are depicted. The sub-components will only be discussed generally in relation to FIG. 1, but will be given detailed treatment in subsequent figures and ensuing descriptions. As indicated, a hospital site 102 includes a plurality of imaging systems 105a-c. Each of the imaging systems 105a-c is linked to corresponding acquisition stations 109a-c. During a cardiac catheterization procedure, a technician, nurse or the physician inputs patient demographic data such as patient name, ID number, treatment required, etc. into a database housed on a computer system linked to an acquisition station.

The data entered by the technician is then stored on the acquisition station 109 in order to identify the particular patient and procedure. The acquisition station 109 is preferably a Personal Computer type of computer based on well-known microprocessors such as those manufactured by Intel and Motorola. The acquisition station preferably runs a WindowsNT operating system although similar computer systems running different operating systems, such as Linux or UNIX, are anticipated to function similarly.

Dynamic video images from patients are captured through the diagnostic imaging system 105, such as those used in conventional cardiac catheterization laboratories. A fall motion video of the catheterization procedure is captured using a camera at the imaging system 105 and the images are preferably converted to DICOM images at the acquisition station 109.

Once a DICOM video of the cardiac catheterization procedure has been captured at the acquisition station, it is transferred, along with patient identification data, over a private high-speed network to a hospital site server 113. The DICOM video images are then temporarily stored on a storage 111 within a hospital site server 113. Once the images have been stored at the site server 113, they are made available for viewing at a plurality of in-hospital review stations 117a,b. In one embodiment, the storage 111 is a conventional hard disk drive.

However, because the captured DICOM images are so large, the hospital site server 113 generates multiple compressed video streams corresponding to each DICOM video. These video streams can be compressed with well-known technologies, such as MPEG-4 and those provided by Apple Quicktime (Apple Corporation) or Microsoft AVI (Microsoft Corporation). Moreover, the compressed videos can be played by conventional Apple Quicktime or Microsoft AVI players available from the respective companies. Other proprietary compression techniques are also within the scope of the invention.

Once the compressed video streams have been created at the hospital site server 113, they are transmitted to a database server 119 within an Internet Data Center (IDC) 121 through a high-speed telecommunications connection. The IDC 121 stores the multiple streams of the compressed video data, along with the pertinent patient and procedure data in a database. Once the compressed streams are transmitted, the site server 113 begins to transmit the large DICOM file to the IDC 121. However, the transfer of the DICOM data is preferably at night, or when demand on the system is determined to be low, such as on a weekend. Thus, the large DICOM images do not interfere with other data transport from a plurality of hospitals to the IDC. In one embodiment the transfer of the DICOM files proceeds immediately as they are available. However they are given a lower priority than the smaller compressed files. The transfer protocol that sends the compressed files preferably supports multiple threads or instances, thus allowing multiple compressed files to be sent to the IDC at the same time. However, in one embodiment, the system only provides one thread for transferring the DICOM files. Accordingly, the larger DICOM files queue up and transmit serially, one after another from the hospital site server to the IDC.

Once the compressed data streams have been transferred to the IDC 121, they are made immediately available for retrieval through a web server 124 to a plurality of web-based clients 129a-c running web-browser software, such as Microsoft Internet Explorer or Netscape Navigator. A typical web-based client 129a, such as a computer, can request and retrieve a patient's compressed files, or lossless DICOM file from either the hospital site server 113, or the IDC 121. Long-term storage is available on the IDC, thus it is anticipated that most queries will be made from the client computers to the IDC for file retrieval.

A computer running a web browser such as Internet Explorer or Netscape Navigator receives web content from the web server 124 at the IDC 121. The web content either invokes a currently available commercial media player such as Apple Quicktime, RealNetworks RealPlayer or Windows Media Player, or may contain an embedded scripted viewer, such as a Java-based viewer programmed for displaying multi-media data streams.

Once the media player is active on the client computer, the multi-media stream will begin playing from the multi-media server 128 at the IDC 121. Thus, any authorized web-based client can access any patient streaming image file from any device that has web-browser software. This allows collaborating diagnosticians to simultaneously view and share patient streaming image files without having to possess the data on physical media.

Because the amount of data storage related to video images is tremendous, a backup data system 130 is provided with a short-term storage 135 and long term system 140 for storing the image data. These components will be discussed in more detail with reference to the following figures.

1. Acquisition Station

Figure 2:
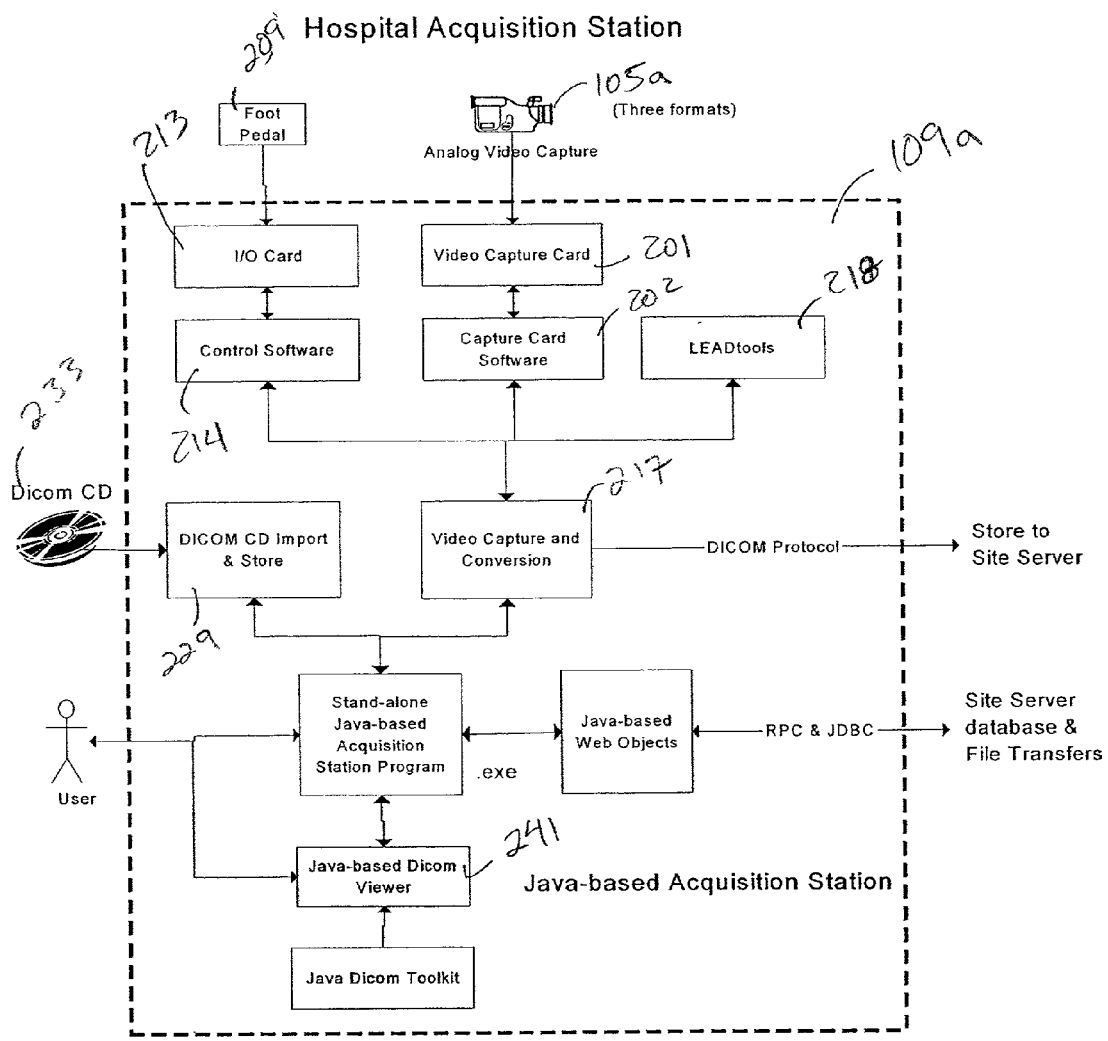
FIG. 2 is a block diagram of a hospital acquisition station, illustrating an image capture system utilizing an analog camera, a system for capturing images from a compact disk, and a system for capturing images from a digital camera.

Referring to FIG. 2, the diagnostic imaging system 105a is used to capture patient video images. In this embodiment, the imaging system 105a is an analog imaging system that converts the captured analog data into a digital format. Thus, the imaging system 105a is linked to a video capture card 201. In one embodiment, the video capture card 201 is a Matrox Genesis LC video frame capture card. While the A/D conversion is preferably performed by a hardware A/D converter on the video capture card, a RAMDISK, or a portion of RAM set aside for exclusive use by an application which simulates hard disk behavior, can be optionally created to assist the hardware A/D conversion. The video capture card is controlled by a series of software libraries 202, such as the Matrox MIL libraries. More information on the Matrox video frame capture cards and corresponding software can be found at http://www.matrox.com.

As the physician uses the imaging system 105a, an on/off switch 209 in the form of a foot pedal 209, sends a change-of-state signal to an input/output board 213. The sensing of the change-of-state signal by the input/output board 213 triggers a message to control software 214 to begin or cease receiving and converting the video images. After receiving an initial message from the input/output board 213, the AID subsystem begins acquiring images until another signal is received from the input/output board 213 to cease acquiring images.

Upon successful acquisition of patient video data, the acquisition station 109 combines the patient video data with the patient demographic information obtained from the lab technician into a valid data set. These steps may be repeated several times during a procedure, and at the conclusion of a procedure, the individual data sets are transferred to the hospital site server 113.

It is preferable for the system to be able to acquire and process data fast enough to keep up in real time with the procedure being performed. One approach to this is utilizing a multi-buffering system, whereby a plurality of frames is moving through various stages of the system simultaneously. For example, as one frame is being acquired by the diagnostic imaging system 105a, a second image is undergoing A/D conversion, while yet another image is being inserted into a data file. This advantageously minimizes memory and allows continuous processing.

A second approach is to pre-allocate sufficient memory for the video capture card to collect enough images to compile a complete data set. This method advantageously ensures that the images are collected and processed. In either case, the images are inserted into a data set, which is a lossless compilation of the acquired image frames. The creation of a valid data set may be performed by DICOM creator software 217. In one embodiment, the DICOM creator software works in conjunction with a software toolkit 218 such as the LEADTOOLS Media Imaging Toolkit (LEAD Technologies, Inc., Charlotte, N.C.).

The DICOM Creator software 217 receives the digital patient video images as image pixel data and incorporates the patient demographic information as appropriate DICOM data tags. The resultant combination is then saved as a valid data set. The acquisition station 109 then temporarily stores the created data set as a DICOMDIR file in a local storage. In addition, the data set may be played through a DICOM Viewer 241, such as a Java-based DICOM viewing program. The DICOMDIR file is additionally sent automatically to the hospital site server 113.

In addition to the method described above, archival image data can be loaded into the system. For example, a recordable optical compact disk, or CD-R 233 may contain previously recorded patient video data. The acquisition station may contain a CD-ROM drive 229 and previously created data sets may be acquired directly from the compact disk 233 and sent to the hospital site server 113.

Additionally, the compact disk 233 may contain digital data in a format other than a DICOM data set, such as when the data were recorded by a diagnostic imaging device not connected to a DICOM compliant system. In this case, the digital data are read from the compact disk 233 and processed through the DICOM creator software 217, and then stored locally 241 and on the hospital site server 113. Additionally, a newly acquired DICOM data set may be saved to the recordable optical compact disk 233 through the CD-R drive 229 installed into the acquisition station. Of course, the CD-R drive could be installed in other stations, such as the review station, hospital site server or other computer linked to the system without departing from the scope of the invention.

It should be realized that image data may also be captured by a digital imaging device, such as a digital camera (not shown). Because the patient image data are already in digital format, the entire A/D subsystem can be bypassed. The digital patient data are processed through the DICOM creator software 217 and the resulting DICOM date set is then sent to the hospital site server 113.

2. Hospital Site Server

Figure 3:
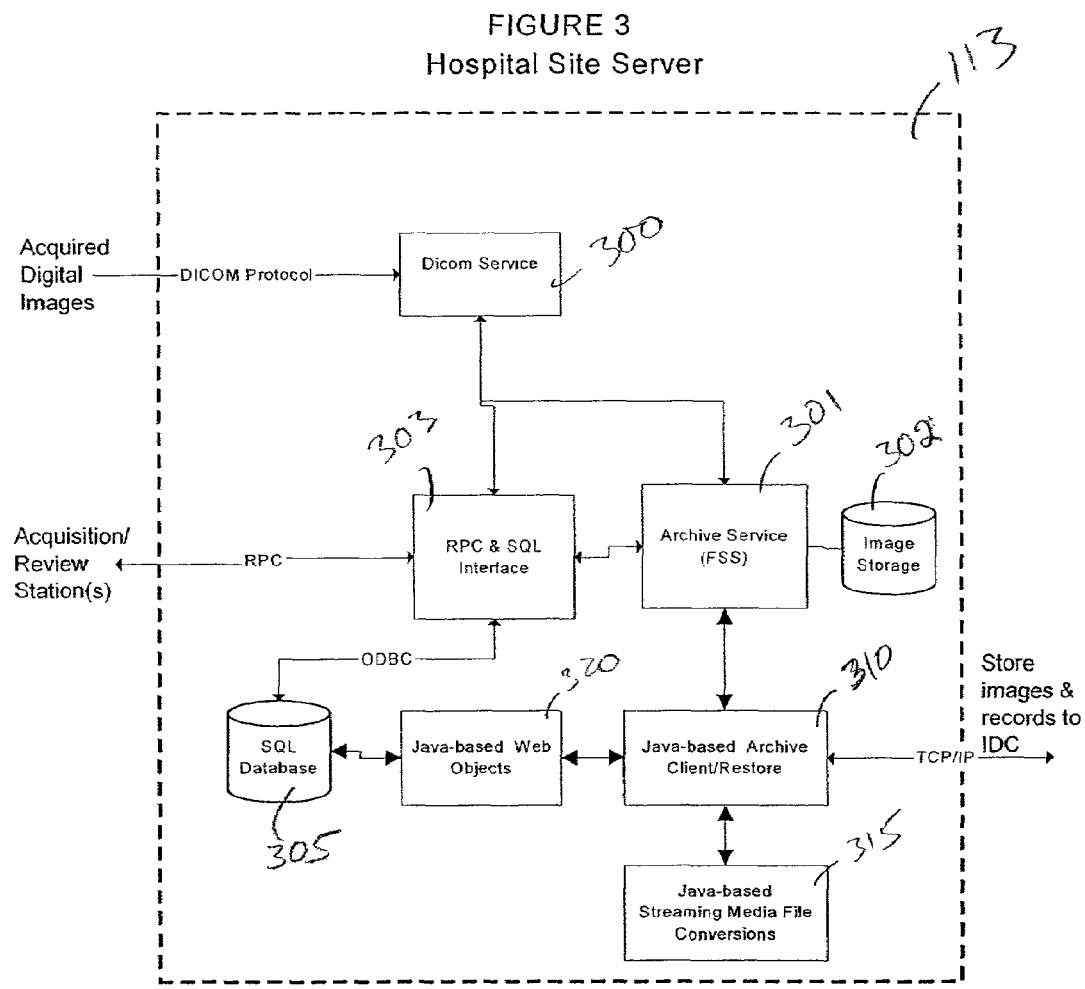
FIG. 3 is a block diagram of one embodiment of a hospital site server.

Reference is now made to FIG. 3, wherein the hospital site server 113 is depicted. The hospital site server 113 receives captured video files from the acquisition station 109 and archives them through an archival service 300 for retrieval from within the hospital. The archival service 300 preferably provides the software necessary for processing incoming video images and storing them to disk. The archival service 300 provides basic image acquisition, local storage and retrieval capabilities. Many image capture and processing systems, such as those compliant with the DICOM standard, are commercially available.

The captured video file is archived through an archival process 301 to a fixed media 302. The video file is preferably retrievable through the interface 303 to an SQL database component 305. The interface 303 provides Remote Procedure Call (RPC) and Structured Query Language (SQL) access to the database 305, thus providing access to the video images stored in the image storage 302.

The in-hospital review station 117 is able to retrieve and view the lossless data sets over a high-speed private network from within the hospital. A diagnostician queries the database 305 for searchable criteria such as patient name, patient ID, test date, and is able to retrieve and view the lossless video data set.

A diagnostician may also view the lossless data set from any device connected to the hospital's high-speed network running web-browser software. A device running web-browser software can access the stored data sets by querying the SQL database just as the above-described review station 117. However, as described above, it is advantageous to provide compressed video image files in addition to the lossless video file.

Preferably, each lossless video file is converted using a media conversion module 315 to at least three different compressed video streams, with each stream designed for delivery to an end user on the Internet at a different bandwidth. The compressed streaming versions are generated at the hospital on the site server to reduce the load on the servers at the Internet Data Center. Once the conversion module 315 converts the lossless video into video files of varying compression, they are stored to the image storage 302.

Thus, end users at the hospital, such as physicians and technicians can manually, or automatically, be presented with the lossless images, or alternatively, one of the compressed versions of the original lossless video data. The Java-based Web Objects 313 serve as the interface between the hospital site server SQL database 320 and the applications running on the networked devices. The Java-based web objects embody the business layer and incorporate all business logic in one place. All software applications requiring business rules invoke the web objects. This design allows modification of business rules or other algorithms in one place. Note that portions of the web-objects business rules are applicable at both the Site Server and IDC, allowing a certain amount of code re-use. A networked device, such as the Review Station, can request a patient data set from the storage 302, at which time the data set is delivered through the server 113 to the requesting device. The diagnostician has access to the lossless data set via the hospital's high-speed private network, such that retrieval time is minimal.

3. Hospital Review Station

Figure 4:
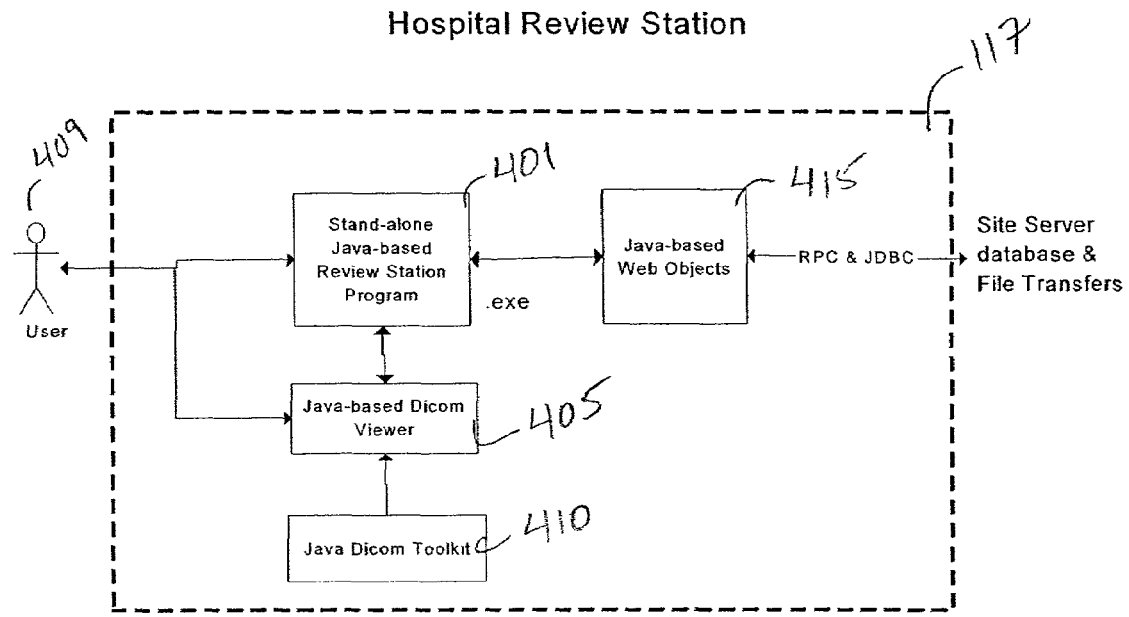
FIG. 4 is a block diagram illustrating one embodiment of an in-hospital review station.

FIG. 4 is a block diagram of the in-hospital review station 117. A user of the review station 409 initiates a stand-alone review station program 401 designed with a graphical user interface to facilitate ease of use. Furthermore, the review station incorporates a video viewer program 405 and toolkit 410, configured with VCR-like controls for forward, reverse, and pause capabilities. When a user invokes the review station program 401, a set of java-based web objects 415 provide access to the SQL database 305 located on the hospital site server 113. The requested video data set is playable through the video viewer 405 at the review station 117. The review station has the advantage of allowing a diagnostician to instantly view lossless data files over the hospital's high-speed network. The data is are transferred through RPC, JDBC, or equivalent protocols, which minimize the data wait time. In an alternate embodiment, the review station viewer is a conventional Apple QuickTime, or similar video-viewing program, including a proprietary custom built viewer, that is incorporated into Internet browser software.

4. Internet Data Center (IDC)

FIG. 5 is a block-diagram of the Internet data center 121, showing the various subsystems. As the hospital site server 113 delivers the patient video files to the IDC 121, they are automatically archived by the backup data system 130. The backup data system comprises an archive service module 500 that is linked to a file server 501. The archive service module 500 provides the instructions for downloading and archiving the lossless video file and video stream files from the site server 113.

The file server 501 is also preferably linked to a RAID image storage 504 and optical or other near-line storage 505 facilities. The archived patient video files that were created as compilations of the separate video files from multiple procedures on a patient are searchable via the SQL database server 119 and the query results are displayed to the user as thumbnail images. As the patient video file is received at the IDC 121, the thumbnail image that was taken from a median frame of the file at the hospital site server is also saved as a thumbnail pointer to that patient video file. As a web-based client 129 requests a particular patient data set by choosing a thumbnail image, the client's bandwidth is automatically detected and the optimally compressed DICOM data set is delivered to that client.

However, a client can also request a file with less compression and better image quality. The content is delivered through the web server 124 as is known in the art along with site specific web content 517. The video data are delivered to the client as streaming media via the multi-media server 128.

In a preferred embodiment, the patient video file is automatically retrieved by the hospital site server 113. For example, when a patient returns to see a physician, the lossless patient video file can be automatically transferred from the backup data system 130 to temporary storage on the hospital site server 113 for immediate retrieval by the physician for review. This alleviates the wait time for a physician to access the file over the Internet once the temporary file is discarded from the hospital site server 113. It also allows the physician to advantageously view the lossless data in place of the streamed lossy image data.

Streaming techniques are known in the art and allow for a loop of video to be retrieved and incrementally shown as each subsequent frame is downloaded, until the full loop is downloaded and viewed.

There are several methods for streaming. Most Internet content is designed to be played through once; hence a typical video loop is downloaded sequentially and then played one time through. Note, however that some video players will show streaming buffers frames as they are downloading and do not wait until all frames have been downloaded. These players download a few frames to a buffer and play those frames as the remaining frames are continuously downloaded.

However, since most medical video loops are designed to by played repeatedly, other streaming techniques are advantageous. For example, embodiments of the invention will stream the first few frames of a video procedure while the system calculates the bandwidth of the link between the player and streaming server. Once the bandwidth is determined, the player advantageously skips a certain number of frames such that the video loop is able to be shown without having to wait for every frame of the video to load. The system continues to download frames and skipping a determined amount of frames before downloading the next frame, and so on. The downloading and skipping process is preferably repeated and the video loop is shown more continuous with each subsequent pass. This allows for the video loop to begin display shortly after the client requests it. However, it should be realized that this embodiment produces a very discontinuous video loop until all the frames are downloaded and displayed in succession.

For example, assuming 100 frames are contained in a video loop, frames 1-3 are first downloaded and displayed. During this initial download, the system calculates that 10 frames must be skipped in order to present the loop without waiting for the subsequent frame to download. The system then serves frames 13, 23, 33, . . . 93. The server will then repeat the loop and display frames 1-3, read, store, and display frame 4, display frame 13, read, store and display frame 14, display frame 23, and so on. The server continues the process until all frames are downloaded and playing in succession.

Another embodiment of the invention provides another method for streaming media to a player. In this embodiment, as the server calculates the client's bandwidth and determines the number of frames to skip in order to show the full loop without having to wait for each successive frame to load, the individual frames are reordered to support sequential downloading. For example, in the above example, rather than skipping 10 frames between each frame downloaded, the entire collection of frames is reordered such that the order of the video loop becomes 1, 10, . . . 100, 2, 11, . . . 91, 3, 12, . . . 92. This becomes more efficient because the system does not have to skip frames between each successive frame download.

Thus, the entire order of the frames is reordered such that the server may deliver the frames sequentially without having to skip a certain number of frames between each frame download. Additionally, the frames are stored into the client's local memory which reduces the time required to save and reload the data to/from a hard drive. For example, a typical image loop may require 50-100 MB of space. If the client computer has 128 MB of memory, the entire image loop may be stored and played from memory, which considerably reduces the time required to receive and play the entire loop. Finally, this described technique allows the server to deliver higher quality images with lower compression and still achieve acceptable download times.

In another embodiment of the invention, the user at the hospital site server 113 is able to tag specific studies that should also be shared with other facilities. These facilities, for example a Clinical Research Organization, will need the lossless data for their studies. The hospital site server passes these tags along with the data to the IDC. The IDC includes a database table that indicates which tags belong to which other sites. Instructions within the IDC then automatically route each DICOMDIR and accompanying ancillary patient data to a Clinical Research Organization that has permission to receive such file. This facilitates the sharing of DICOM data without manual intervention required to download and save the data. Furthermore, a Clinical Research Organization will have the requested files available when they are ready to view them. Additionally, a patient that is entered into several clinical trials might have his cardiac data sent to multiple clinical research organizations.

While the above description contains much specificity, these should be construed as illustrations and not limitations on the scope of the invention. Additionally, there are numerous variations of the foregoing description not contained herein that do not depart from the scope of the invention as claimed. Accordingly, the scope of the invention is limited to the following claims.

What is claimed is:

1. A system for processing patient video images, comprising:
   a medical services site that includes an acquisition station, a review station, a site sever, and a local network for transporting the patient video images between the acquisition station, review station, and site server;
   said acquisition station for collecting the patient video images;
   said site sever for receiving the patient video images from said acquisition station over the local network and storing the patient video images;
   the review station for retrieving patient video images from the site server over the local network and displaying the patient video images to a diagnostician;
   an internet data center in communication with said site sewer and receiving the patient video images transmitted by the site server over an internet communication network;
   said internet data center including a web server and a database server;
   said database server storing the patient video images; and
   a web-based client for receiving said patient video images from the web server of said internet data center over said internet communication network;
   wherein the web server transmits frames of the patient video images to the web-based client in which intervening frames of the patient video images have been skipped, the web-based client displaying the received frames, and then later the web server transmits the skipped frames of patient video images, which the web-based client then displays with the previously received frames.

2. The system of claim 1, wherein the site server generates different compressed video files having different levels of compression.

3. The system of claim 2, wherein said internet data center includes means for detecting a bandwidth of the web-based client and then transmits the patient video images with a compression determined in response to the detected bandwidth.

4. The system of claim 1, further comprising a backup data system that comprises at least one storage facility for storing said patient video images.

5. The system of claim 4, wherein said multi-media server receives said patient video images from said backup data system and delivers them to the web-based client as streaming media.

6. The system of claim 1,
   wherein said internet data center further comprises a backup data system, the backup data system automatically transferring patient video images to the site server in response to a corresponding patient returning to the medical services site.

7. The system of claim 6, wherein said site server is configured to create a thumbnail image of said patient video, wherein said thumbnail image is derived from a median frame in said patient video.

8. The system of claim 7, including an image backup data system that is configured to retrieve a specified patient file upon request.

9. The system of claim 8, further comprising instructions for receiving the patient video image file upon selection of the thumbnail image by a user.

10. The system of claim 1, wherein the site server and/or the database server store both lossless patient video images and video images that have been compressed using a lossy compression.

11. The system of claim 1, wherein the site server transmits the patient video images to the internet data center at night and on weekends.

12. The system of claim 1, wherein the site sewer and/or the internet data center transmit the patient video images to a clinical research organization.

13. The system of claim 1, wherein said acquisition station is located in a cardiac catheterization lab to receive images from a catheterization camera.

14. The system of claim 1, wherein said acquisition station is located in a catheterization lab to receive images from an x-ray angioplasty machine.

* * * * *

UNITED STATES PATENT AND TRADEMARK OFFICE
CERTIFICATE OF CORRECTION

| | | |
|---|---|---|
| PATENT NO. | : 7,257,832 B2 | Page 1 of 1 |
| APPLICATION NO. | : 09/974406 | |
| DATED | : August 14, 2007 | |
| INVENTOR(S) | : John A. Beane, Larry J. Heminger and Robert M. Stone | |

It is certified that error appears in the above-identified patent and that said Letters Patent is hereby corrected as shown below:

In Claim 1, column 15, line 33, delete "sever" and insert --server--.

In Claim 1, column 15, line 38, delete "sever" and insert --server--.

In Claim 1, column 15, line 45, delete "sewer" and insert --server--.

Signed and Sealed this

Twenty-seventh Day of November, 2007

JON W. DUDAS
*Director of the United States Patent and Trademark Office*